(12) United States Patent
Niland et al.

(10) Patent No.: US 7,708,013 B2
(45) Date of Patent: May 4, 2010

(54) APPARATUS AND METHOD FOR DELIVERING WATER VAPOR TO A GAS

(75) Inventors: William F. Niland, Arnold, MD (US); Owen S. Bamford, Linthicum, MD (US); Felino V. Cortez, Jr., Bowie, MD (US)

(73) Assignee: Vapotherm, Inc., Stevensville, MD (US)

( * ) Notice: Subject to any disclaimer, the term of this patent is extended or adjusted under 35 U.S.C. 154(b) by 0 days.

(21) Appl. No.: 10/810,768

(22) Filed: Mar. 26, 2004

(65) Prior Publication Data
US 2004/0245658 A1 Dec. 9, 2004

Related U.S. Application Data

(63) Continuation-in-part of application No. 10/149,356, filed as application No. PCT/US00/33346 on Dec. 8, 2000, now Pat. No. 7,314,046.

(51) Int. Cl.
*A61M 16/00* (2006.01)
*A61M 15/00* (2006.01)
(52) U.S. Cl. ............................. 128/201.13; 128/203.16; 128/203.26
(58) Field of Classification Search ............ 128/201.13, 128/203.16, 203.17, 203.26, 204.17, 911, 128/203.15
See application file for complete search history.

(56) References Cited

U.S. PATENT DOCUMENTS 3,491,754 A * 1/1970 Weese ................... 128/204.17
3,616,796 A 11/1971 Jackson
3,638,926 A 2/1972 Melville et al.
3,864,440 A * 2/1975 Giocoechea ............. 261/122.1
3,871,373 A 3/1975 Jackson
3,912,795 A * 10/1975 Jackson ...................... 261/36.1
3,923,057 A * 12/1975 Chalon .................. 128/203.16

(Continued)

FOREIGN PATENT DOCUMENTS

EP 0 009 543 A1 4/1980

(Continued)

OTHER PUBLICATIONS

International Search Report for PCT/US00/33346, search date May 29, 2001, the corresponding international application for the parent U.S. Appl. No. 10/149,356, filed Jan. 29, 2003 for the above-identified U.S. patent application.

(Continued)

*Primary Examiner*—Danton DeMille
(74) *Attorney, Agent, or Firm*—RatnerPrestia

(57) ABSTRACT

An apparatus for delivering water vapor to a gas is formed from a plurality of hollow fiber membranes each defining a passage for the flow of gas from an upstream end of the passage and enclosed by an enclosure. The hollow fiber membranes have a combined surface area in the range of about 90 square centimeters to about 110 square centimeters. The enclosure contains an air inlet positioned to direct air to the upstream end of each of the passages of the hollow fiber membranes and an air outlet positioned to direct air from the downstream end of each of the passages of the hollow fiber membranes. The enclosure preferably has a water inlet positioned to direct water toward the outer surfaces of the hollow fiber membranes and a water outlet positioned to direct water from the enclosure.

24 Claims, 4 Drawing Sheets

U.S. PATENT DOCUMENTS

| | | | |
|---|---|---|---|
| 3,944,635 A * | 3/1976 | Siegenthaler | 261/62 |
| 3,982,095 A | 9/1976 | Robinson | |
| 4,010,748 A | 3/1977 | Dobritz | |
| 4,026,285 A * | 5/1977 | Jackson | 128/200.17 |
| 4,028,444 A | 6/1977 | Brown et al. | |
| 4,036,919 A | 7/1977 | Komendowski et al. | |
| 4,051,205 A | 9/1977 | Grant | |
| 4,060,576 A | 11/1977 | Grant | |
| 4,110,419 A * | 8/1978 | Miller | 261/142 |
| 4,134,940 A * | 1/1979 | Sherman | 261/124 |
| 4,137,940 A | 2/1979 | Faisandier | |
| 4,163,371 A | 8/1979 | Groninger | |
| 4,172,105 A | 10/1979 | Miller et al. | |
| 4,201,204 A | 5/1980 | Rinne et al. | |
| 4,204,535 A * | 5/1980 | Pohlmann | 128/202.13 |
| 4,232,667 A * | 11/1980 | Chalon et al. | 128/203.26 |
| 4,249,527 A * | 2/1981 | Ko et al. | 128/204.18 |
| 4,303,601 A | 12/1981 | Grimm et al. | |
| 4,319,566 A | 3/1982 | Hayward et al. | |
| 4,324,238 A | 4/1982 | Genese et al. | |
| 4,328,793 A * | 5/1982 | Martin | 600/22 |
| 4,338,267 A * | 7/1982 | Riuli et al. | 261/121.1 |
| 4,350,647 A * | 9/1982 | de la Cruz | 261/65 |
| 4,372,306 A | 2/1983 | Genese et al. | |
| 4,381,267 A * | 4/1983 | Jackson | 261/104 |
| 4,401,114 A * | 8/1983 | Lwoff et al. | 128/200.14 |
| 4,463,755 A * | 8/1984 | Suzuki | 128/204.18 |
| 4,481,944 A * | 11/1984 | Bunnell | 128/204.18 |
| 4,495,944 A | 1/1985 | Brisson et al. | |
| 4,500,480 A | 2/1985 | Cambio, Jr. | |
| 4,527,557 A | 7/1985 | DeVries et al. | |
| 4,621,632 A | 11/1986 | Bartels et al. | |
| 4,621,633 A | 11/1986 | Bowles et al. | |
| 4,632,677 A | 12/1986 | Blackmer | |
| 4,682,010 A * | 7/1987 | Drapeau et al. | 392/488 |
| 4,686,354 A * | 8/1987 | Makin | 392/472 |
| 4,708,831 A | 11/1987 | Elsworth et al. | |
| 4,715,998 A | 12/1987 | Clow | |
| 4,722,334 A | 2/1988 | Blackmer et al. | |
| 4,773,410 A * | 9/1988 | Blackmer et al. | 128/203.26 |
| 4,801,385 A * | 1/1989 | Sachtler et al. | 210/644 |
| 4,829,998 A * | 5/1989 | Jackson | 128/203.12 |
| 4,886,055 A * | 12/1989 | Hoppough | 128/200.14 |
| 4,911,157 A * | 3/1990 | Miller | 128/200.21 |
| 4,921,642 A | 5/1990 | LaTorraca | |
| 4,943,704 A | 7/1990 | Rabenau et al. | |
| 4,953,546 A | 9/1990 | Blackmer et al. | |
| 4,955,372 A * | 9/1990 | Blackmer et al. | 128/203.16 |
| 4,967,744 A * | 11/1990 | Chua | 128/204.18 |
| 5,031,612 A | 7/1991 | Clementi | |
| 5,036,847 A | 8/1991 | Boussignac et al. | |
| 5,062,145 A | 10/1991 | Zwaan et al. | |
| 5,063,994 A | 11/1991 | Verkaart | |
| 5,097,898 A | 3/1992 | Verkaart | |
| 5,101,820 A * | 4/1992 | Christopher | 128/204.18 |
| 5,109,471 A | 4/1992 | Lang | |
| 5,195,515 A | 3/1993 | Levine | |
| 5,218,833 A | 6/1993 | Newbold | |
| 5,236,586 A * | 8/1993 | Antoni et al. | 210/321.8 |
| 5,255,674 A * | 10/1993 | Oftedal et al. | 128/203.16 |
| 5,271,391 A * | 12/1993 | Graves | 128/207.18 |
| 5,348,691 A * | 9/1994 | McElroy et al. | 261/36.1 |
| 5,349,946 A * | 9/1994 | McComb | 128/203.17 |
| 5,394,867 A | 3/1995 | Swann | |
| 5,396,884 A * | 3/1995 | Bagwell et al. | 128/200.21 |
| 5,617,847 A | 4/1997 | Howe | |
| 5,738,808 A * | 4/1998 | Iwamoto | 261/104 |
| 5,769,071 A | 6/1998 | Turnbull | |
| 5,868,133 A | 2/1999 | DeVries et al. | |
| 5,890,490 A * | 4/1999 | Aylsworth et al. | 128/203.12 |
| 5,901,705 A | 5/1999 | Leagre | |
| 6,050,260 A * | 4/2000 | Daniell et al. | 128/204.22 |
| 6,095,505 A | 8/2000 | Miller | |
| 6,102,037 A | 8/2000 | Koch | |
| 6,129,082 A | 10/2000 | Leagre | |
| 6,332,462 B1 * | 12/2001 | Krohn | 128/204.15 |
| 6,367,472 B1 * | 4/2002 | Koch | 128/203.12 |
| 6,397,841 B1 | 6/2002 | Kenyon et al. | |
| 6,457,472 B1 | 10/2002 | Schwartz et al. | |
| 6,474,335 B1 * | 11/2002 | Lammers | 128/205.12 |
| 6,474,628 B1 * | 11/2002 | Stroh et al. | 261/99 |
| 6,516,801 B2 | 2/2003 | Boussignac | |
| 6,526,970 B2 | 3/2003 | DeVries et al. | |
| 6,536,428 B1 | 3/2003 | Smith et al. | |
| 6,653,012 B2 | 11/2003 | Suzuki et al. | |
| 6,739,338 B2 * | 5/2004 | Tanhehco et al. | 128/205.24 |
| 6,769,431 B2 | 8/2004 | Smith et al. | |
| 6,786,475 B2 * | 9/2004 | Salter et al. | 261/62 |
| 6,877,510 B2 | 4/2005 | Nitta | |
| 6,904,911 B2 | 6/2005 | Gibertoni | |
| 6,953,354 B2 | 10/2005 | Edirisuriya et al. | |
| 6,976,489 B2 * | 12/2005 | Mantell et al. | 128/204.17 |
| 6,988,497 B2 | 1/2006 | Levine | |
| 7,086,399 B2 | 8/2006 | Makinson et al. | |
| 7,140,367 B2 | 11/2006 | White et al. | |
| 7,146,979 B2 | 12/2006 | Seakins et al. | |
| 2002/0195104 A1 | 12/2002 | Fini et al. | |
| 2003/0209246 A1 | 11/2003 | Schroeder et al. | |
| 2004/0016428 A9 | 1/2004 | Lurie | |
| 2004/0221844 A1 | 11/2004 | Hunt | |
| 2005/0121038 A1 | 6/2005 | Christopher | |
| 2005/0178383 A1 | 8/2005 | Mackie et al. | |
| 2006/0037613 A1 | 2/2006 | Kwok et al. | |
| 2006/0118111 A1 | 6/2006 | Pelerossi et al. | |
| 2007/0175473 A1 | 8/2007 | Lewis et al. | |

FOREIGN PATENT DOCUMENTS

| | | |
|---|---|---|
| EP | 0 062 913 A1 | 10/1982 |
| EP | 0 359 531 A2 | 3/1990 |
| FR | 2164873 | 8/1973 |
| FR | 2 311 558 | 12/1976 |
| WO | WO 86/02276 | 4/1986 |

OTHER PUBLICATIONS

Abstract—Effect of Vapotherm$^R$, A High-Flow Humidified $O^2$ Delivery Device, On Breathing in COPD Patterns During Exercise, Nugent T. Vance, G. Criner GJ, Chatlia W. Div Plum and Crit Care, Temple School of Medicine, Phila., PA, (Reprinted from American Journal of Respiratory and Critical Care Medicine vol. 165, No. 8, Part 2, Apr. 2002, p. A592.

International Search Report for PCT/US05/09556, search date Jul. 6, 2005.

* cited by examiner

APPARATUS AND METHOD FOR DELIVERING WATER VAPOR TO A GAS

This application is a Continuation-In-Part of application Ser. No. 10/149,356, filed Jan. 29, 2003, now U.S. Pat. No. 7,341,046 which is a National Phase of PCT/US00/33346 filed Dec. 8, 2000.

FIELD OF THE INVENTION

The present invention relates to an apparatus and method for delivering water vapor to a gas. More particularly, this invention relates to a low flow vapor transfer cartridge that optionally allows water to pass into a gas stream at gas flow rates ranging from about 1 liter per minute to about 8 liters per minute without a transfer of water in a liquid state. The low flow cartridge acts as a complete or partial barrier against bacteria while simultaneously allowing the passage of water vapor.

BACKGROUND OF THE INVENTION

It has been recognized that the delivery of oxygen and oxygen-enriched air to the respiratory tract of a patient often results in discomfort to the patient, especially when the air is delivered over an extended period of time. It has also been recognized that the delivery of air having relatively low absolute humidity can result in respiratory irritation.

Several devices have been proposed to overcome these problems. U.S. Patent Publication No. 2003/0209246A1, the entire disclosure of which is incorporated herein by reference, describes embodiments of an apparatus and method for respiratory tract therapy adapted to heat and humidify air and to deliver heated and humidified air to the respiratory tract of a human patient. Devices such as those disclosed in U.S. Patent Publication No. 2003/0209246A1 represent an improvement over prior art devices.

Nevertheless, there remains a need for devices adapted to deliver supplemental breathing gases at low continuous flow rates such as flow rates less than about 5 liters per minute at high relative humidities such as about 100% relative humidity and in an elevated temperature range such as a temperature range from about 33° C. to about 43° C. There also remains a need for delivering gas warmed and humidified with water vapor at flow rates ranging from about 1 liter per minute or lower to about 8 liters per minute or higher.

SUMMARY OF THE INVENTION

The present invention, according to one aspect, provides an apparatus for delivering water vapor to a gas. The apparatus includes a plurality of hollow fiber membranes each defining a passage for the flow of gas from an upstream end of each passage to a downstream end of each passage. The enclosure encloses the hollow fiber membranes and has an air inlet positioned to direct air to the upstream end of each of the passages of the hollow fiber membranes. An air outlet is positioned to direct air from the downstream end of each of the passages of the hollow fiber membranes. The enclosure has a water inlet positioned to direct water toward outer surfaces of the hollow fiber membranes and a water outlet positioned to direct water from the enclosure. The hollow fiber membranes have a combined surface area in a range of about 90 square centimeters to about 110 square centimeters.

Another aspect of the present invention provides a method for heating and humidifying a gas. The method includes delivering a gas through a plurality of hollow fiber membranes at a flow rate of about 1 liter per minute to about 8 liters per minute. Outer surfaces of the hollow fiber membranes are contacted with water at a temperature of about 33° C. to about 43° C. The combined surface area of the hollow fiber membranes is maintained between about 90 square centimeters and about 110 square centimeters.

According to yet another aspect, the present invention provides a system for delivering humidified gas to a patient. The system includes means for receiving water, means for receiving gas, and an apparatus in flow communication with said water receiving means and said gas receiving means that is configured to deliver vapor from water to gas. The apparatus includes hollow fiber membranes and an enclosure enclosing the hollow fiber membranes. The hollow fiber membranes have a combined surface area in the range of about 90 square centimeters to about 110 square centimeters.

BRIEF DESCRIPTION OF THE DRAWINGS

A more complete appreciation of the subject matter of the present invention and the various advantages thereof can be realized by reference to the following detailed description, in which reference is made to the accompanying drawings which.

DETAILED DESCRIPTION OF THE INVENTION

Figure 1:
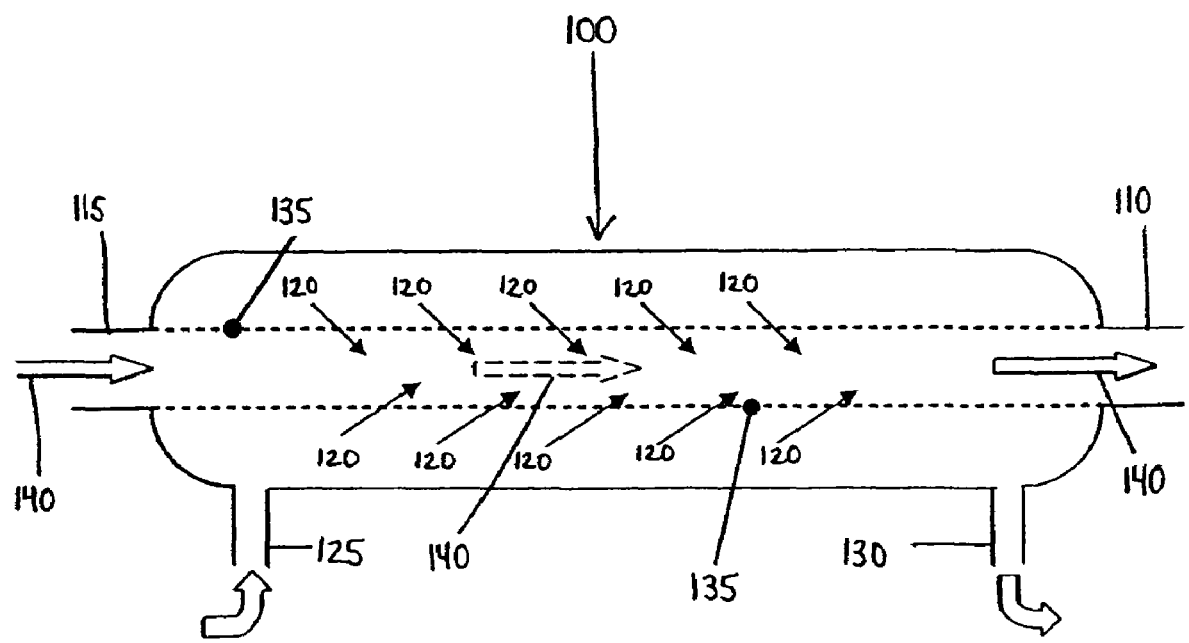
FIG. 1 is a schematic diagram of an embodiment of a vapor transfer cartridge according to aspects of this invention.
Figure 2:
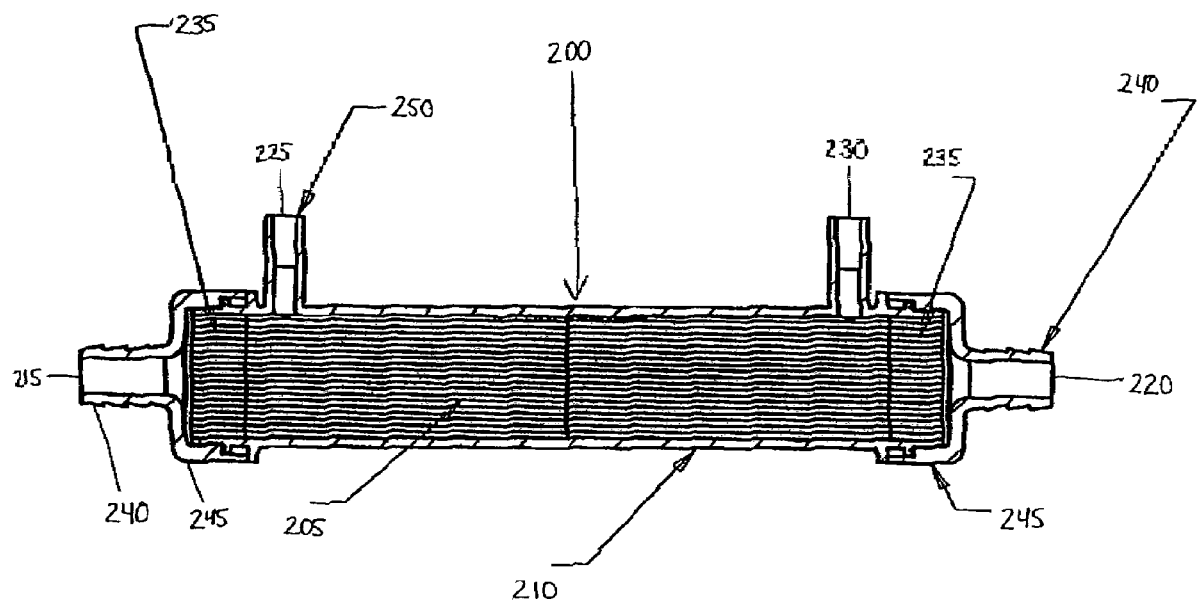
FIG. 2 is a cross-sectional side view of another embodiment of a vapor transfer cartridge according to aspects of this invention.
Figure 3:
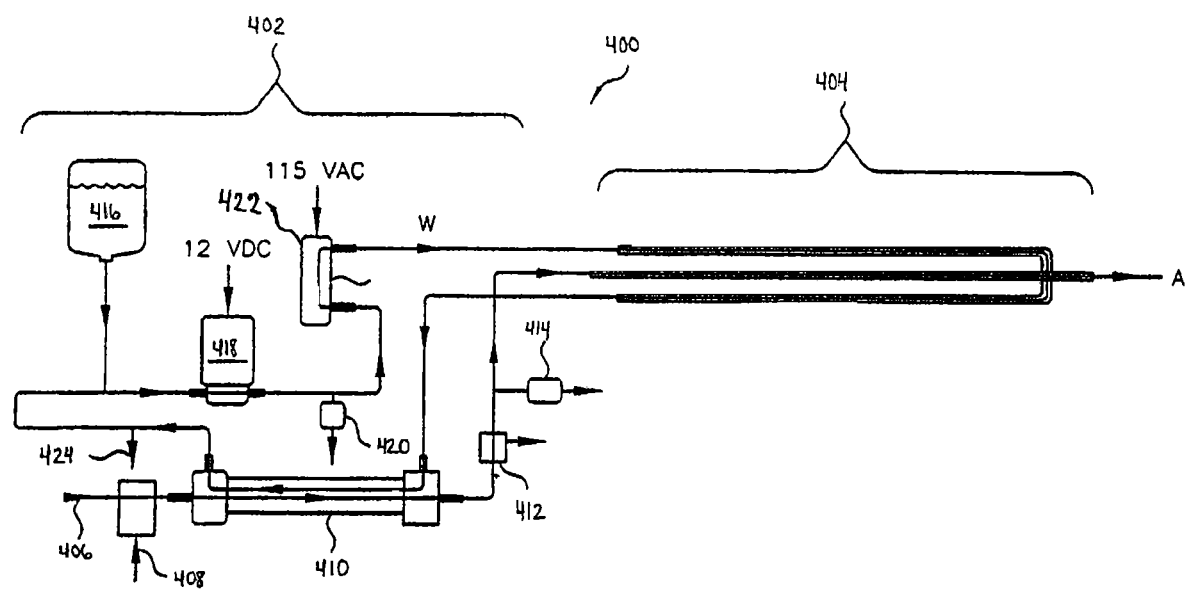
FIG. 3 is a schematic diagram of another embodiment of a system according to aspects of this invention.

In the detailed description which follows, the features of the present invention will be described in connection with the delivery of humidified gas to a patient. FIG. 3 provides a schematic illustration of embodiments of system, in their entirety. FIGS. 1 and 2 illustrate embodiments of vapor flow cartridges that can be used in systems such as the system illustrated in FIG. 3.

Referring generally to the figures, an apparatus 100, 200 is provided for delivering water vapor to a gas. The apparatus 100, 200 includes a plurality of hollow fiber membranes 135, 205 each defining a passage for the flow of gas from an upstream end of said each passage to a downstream end of said each passage. An enclosure 210 encloses the hollow fiber membranes 135, 205 and has an air inlet 115, 215 positioned to direct air to the upstream end of each of the passages of the hollow fiber membranes 135, 205. An air outlet 110, 220 is positioned to direct air from the downstream end of each of the passages of the hollow fiber membranes 135, 205. The enclosure 210 has a water inlet 125, 225 positioned to direct water toward outer surfaces of the hollow fiber membranes 135, 205 and a water outlet 130, 230 positioned to direct water from the enclosure 210. The hollow fiber membranes 135, 205 have a combined surface area in a range of about 90 square centimeters to about 110 square centimeters.

In an exemplary use, gas is delivered through hollow fiber membranes 135, 205 at a flow rate of about 1 liter per minute to about 8 liters per minute. Outer surfaces of the hollow fiber membranes 135, 205 are contacted with water at a temperature of about 33° C. to about 43° C. The combined surface area of the hollow fiber membranes 135, 205 is maintained between about 90 square centimeters and about 110 square centimeters.

The invention also provides a system 400 for delivering humidified gas to a patient. The system 400 includes means for receiving water, means for receiving gas, and an apparatus 100, 200 in flow communication with said water receiving means and said gas receiving means that is configured to deliver vapor from water to gas. The apparatus 100, 200 includes hollow fiber membranes 135, 205 and an enclosure 210 enclosing the hollow fiber membranes 135, 205. The hollow fiber membranes 135, 205 have a combined surface area in the range of about 90 square centimeters to about 110 square centimeters.

Though reference is made to the delivery of heated and humidified air to a patient according to exemplary embodiments of this invention, this invention is not limited to the delivery of air. Also, air or another gas may or may not be heated prior to delivery to the patient (though it preferably is heated). Finally, humidification of air or another gas is accomplished by delivering water vapor to the gas according to exemplary embodiments of this invention, but the delivery of other vapors to the gas in addition to or instead of water vapor is also contemplated.

A heat-moisture exchange cartridge, which will be described later in further detail, is preferably accessible for service without disassembly or removal of the system from an IV pole. One example of a cartridge that can be used in an apparatus according to this invention is provided by Vapotherm, Inc. under part number VT01-B. Other configurations of this cassette may be considered in order to increase surface area and reduce pressure drop. The hollow fibers of one preferred cartridge have a wall thickness of about 55 to about 60 microns. Other hollow fibers can of course be utilized.

Referring now to FIG. 3, exemplary features of another apparatus adapted for delivering heated and humidified gas will now be described. Referring to the schematic representation provided in FIG. 3, an apparatus 400 includes a supply unit assembly 402 and a delivery tube assembly 404, which is adapted to be removably attached to supply unit assembly 402. Supply unit assembly 402 is provided with an inlet 406 for receiving gas from a wall source or from a compressor or a tank or other source. In a lower flow application, the gas is most preferably provided with a flow rate from about 1 to about 8 l/min, though higher and lower flow rates are contemplated as well.

Down stream from inlet 406 is a gas shutoff solenoid valve 408 to prevent gas flow when desired. An exchanger 410 is provided to humidify the gas by means of counter-current flow of water and gas through the exchanger 410. A leak detector 412 and a pressure transducer 414 are provided down stream of exchanger 410. The gas then travels outwardly through delivery tube assembly 404 in order provide a supply of heated, humidified gas as indicated at "A".

Supply unit assembly 402 is configured to receive water from a water bag 416. A pump 418, which can be provided with a 12VDC power supply, urges the water through supply unit assembly 402. A pressure transducer 420 is provided down stream of pump 418 to sense the pressure of the water in the system. The water is then heated in heater 422, which can be provided with a 115VAC power supply. The water, as indicated at "W," advances through supply unit assembly 402 into delivery tube assembly 404. Water W is preferably delivered from supply unit assembly 402 at a flow rate of about 0.6 l/min., and at a pressure of about 8 psi, though higher and lower flow rates and pressures are contemplated as well.

The heated water flows through the delivery tube assembly 404 in a manner that will be described in further detail later. The water then returns to supply unit assembly 402 for flow through exchanger 410. The temperature of the water is sensed at a location down stream from the exchanger 410. The water then repeats the circuit through the system in a circulating manner. Water from water bag 416 supplements the recirculating water.

FIG. 1 illustrates an exemplary embodiment of a low flow cartridge 100 for delivering water vapor to a gas. The cartridge 100 is configured for use in systems such as system 400 illustrated in FIG. 3, respectively. The cartridge 100 is used to humidify an air stream 140 that passes through hollow fiber membranes 135 of the cartridge 100 while warmed water is circulating on the exterior of the hollow fiber membranes 135. The cartridge 100 contains a plurality of hollow fiber membranes 135, each defining a passage for the flow 140 of gas from an upstream end of the passage to a downstream end of the passage. Gas enters the cartridge at an air inlet 115 at an exemplary pressure rating of about 10 psi and an inlet temperature of about 17° C. to about 27° C. Air is delivered through a plurality of hollow fiber membranes 135 at a flow rate of about 1 liter per minute to about 8 liters per minute. The pressure drop through the hollow fiber membranes 135 is desirably less than about 100 mmHg at 5 lpm.

Water enters the cartridge 100 at the water inlet 125 with a preferred inlet pressure up to about 90 mmHg and contacts the outer surfaces of the hollow fiber membranes 135 with water at a temperature of about 33° C. to about 43° C. The water flows through the spaces between the outer surfaces of the hollow fiber membranes 135 and passes through pores (at 120) in the hollow fiber membranes 135 to deliver vaporized water to the stream 140 of gas within the membranes 135.

The flow of gas at 140 as it becomes moisturized moves downstream to the end of the passage 140 where air exits the cartridge at the air outlet 110. Water is circulated through the interior region of the cartridge 100 (around the outer surfaces of the hollow fiber membranes), and circulating water exits the cartridge 100 at the water outlet 130.

An exemplary embodiment of the present invention limits the transfer of water vapor to breathing gas to the point where no water is present in the liquid state in the breathing gas, while preferably maintaining a relative humidity of about 100%. Relative humidity levels are optionally reduced to about 95% with an air inlet of 5 liters per minute, while not allowing the passage of liquid water.

In another embodiment, the preferred cartridge 100 design is such that the walls of the hollow fiber membranes 205 are preferably sized to allow enough water vapor to pass through to completely saturate gas flows up to about 8 liters per minute with vapor, while holding back liquid water. Performance can be defined by applying a water pressure to the outside of the hollow fiber membranes 205 and measuring (1) the time taken for liquid water to penetrate hollow fiber membranes 205 and (2) the rate of water flow through the hollow fiber membranes 205 after penetration has occurred. In a preferred embodiment, performance is adequate if at a static pressure of 47 mmHg, penetration takes at least one hour, and water flow thereafter is less than 0.21 mL/min.

FIG. 2 illustrates the compartmental structure of the low flow cartridge to 200. The enclosure 210 encloses hollow fiber membranes 205 surrounded by temperature-controlled circulating water. In an exemplary embodiment, the enclosure 210 may partially be formed from a polycarbonate material. The enclosure 210 comprises a water inlet 225 positioned to direct water toward outer surfaces of the hollow fiber membranes 205 and a water outlet 230 positioned to direct water from the enclosure. Water molecules diffuse through the hollow fiber membranes 205 into the lumen where they are swept up by breathing gas passing along the hollow fiber membranes 205. The enclosure 210 has an air inlet 215 positioned to direct air to the upstream end of each of the passages of the hollow fiber membranes 205 and an air outlet 220 positioned to direct air from the downstream end of each of the passages of the hollow fiber membranes 205.

The cartridge 200 is configured to limit the transfer of water vapor to breathing gas to the point where little or no water is present in the liquid state in the breathing gas. According to a preferred embodiment, no water is present in the liquid state in the breathing gas, and the cartridge is configured to maintain a relative humidity of about 100%.

In lower flow applications (e.g., with breathing gas flows of about 1 lpm to about 8 lpm), it has in the past been difficult to reduce or prevent the flow of liquid water into the breathing gas. More specifically, because of the low flow rate of the breathing gas, there can be an accumulation of water vapor in the breathing gas and the resulting formation of liquid water in the breathing gas.

It has been discovered, however, that the flow of liquid water into breathing gas can be reduced or eliminated by reducing the surface area of the cumulative outer surfaces of the hollow fiber membranes 205. While such a reduction of surface area has been discovered to be beneficial for reducing the passage of liquid water, undue reduction of surface area prevents adequate passage of water vapor to properly humidify the breathing gas. Most preferably, it is desired to provide relative humidity levels in the range of about 95% to about 100% while not allowing the passage of liquid water.

It has been discovered that the preferred rate at which water vapor diffuses through hollow fiber membranes 205 into the stream of breathing gas depends on at least one of two main variables, namely the surface area available for diffusion, and the pressure gradient across the wall of hollow fiber membranes 205. The pressure gradient is the difference between the water pressure outside and the gas pressure inside the hollow fiber membranes 205. Water pressure can be regarded as constant. At low flow gas rates, the gas pressure is also low and hence the gradient favors increased water diffusion into the gas stream. Moreover, the lower gas flow has a reduced capacity to carry water vapor. The combined effect is a tendency for more water to diffuse through the hollow fiber membranes 205 than that which can be carried away as a vapor. The result is that the gas stream can accumulate drops of liquid water which are then carried into the patient's airway. In order to reduce the amount of water entering the gas stream, it has been discovered that the surface area available for diffusion can be reduced. The reduction of the surface with present cartridge 100, 200 design is accomplished by reducing the number of hollow fiber membranes 205. More specifically, it has been discovered that water transfer performance within the effective range can be achieved using approximately 250 hollow fiber membranes with a total surface area in a range of about 90 square centimeters to 110 square centimeters, preferably about 100 square centimeters. The foregoing surface areas have been discovered to be especially desirable for flow rates between about 1 lpm and about 8 lpm.

The surface area of the cartridge 200 is optionally reduced by reducing the number of hollow fiber membranes 205, thus reducing the amount of combined surface area of the hollow fiber membranes 205 for gas flow and vapor exchange. Alternatively, the outer diameter and/or length of the hollow fiber membranes 205 is optionally decreased to reduce the surface area. Accordingly, the reduction of the surface area can be accomplished by selecting the number of fibers, by changing the dimensions of the fibers, or a combination of the foregoing.

In an exemplary embodiment, an array of hollow fiber membranes 205 are formed from a polymeric material and comprise polysulfone. They may however be formed from a non-polymeric material. Hollow fiber membranes 205 are connected to caps 245 positioned at the end of the enclosure 210. Urethane potting material 235 can be disposed at each end of the cartridge 200 to position hollow fiber to membranes 205 securely in the enclosure 210 and to completely or substantially prevent the mixing of air and liquid water in the cartridge.

The air inlet 215 and air outlet 220 of the enclosure 210 are defined by caps 245 positioned at end portions of the enclosure 210. These end caps 245 are secured over the enclosure 210 at both ends to enclose the interior of the cartridge 200, but are optionally detachable. The end caps 245 may be composed of polycarbonate or a similar type material. Each of the end caps 245 comprises a hose barb 240, which hose barbs 240 are therefore disposed at both ends of the cartridge 210 to facilitate connection of the cartridge 200 to the entire system (i.e., to conduits through which gas is delivered to and from the cartridge). The hose barbs 245 therefore define the air inlet 215 at one end and the air outlet 220 at the opposite end. The cartridge 200 is optionally provided with a luer connection 250 to define each of the water inlet 225 and the water outlet 230 and to bridge the cartridge 200 to another outside device (i.e., to conduits through which water is delivered to and from the cartridge).

As mentioned previously, the hollow fiber membranes 205 are desirably configured to resist water breakthrough for at least one hour when gas flow is absent and the static water pressure is about 47 mmHg. Each of the hollow fiber membranes 205 is configured such that a water flux after an initial water breakthrough does not exceed about 0.21 milliliters per minute at a static water pressure of 47 mmHg. The hollow fiber membranes, and the cartridges in which they are mounted, can therefore be tested to ensure that they are suitable for low flow applications.

In yet another exemplary embodiment, the cartridge 200 has a length ranging from about 6 inches to about 6.5 inches and a width ranging from about 1 inch to about 1.5 inches. The ends of the cartridge 200 are desirably provided with ⅜ inch hose barbs 240. The case side connections are preferably approximately ⅝ of an inch long and have an inner diameter of about ¼ inch. While these dimensions are provided for purposes of illustration, it will be recognized that a wide variety of shapes, sizes and configurations can be selected and that the invention is not limited to any particular size or shape.

Figure 4:
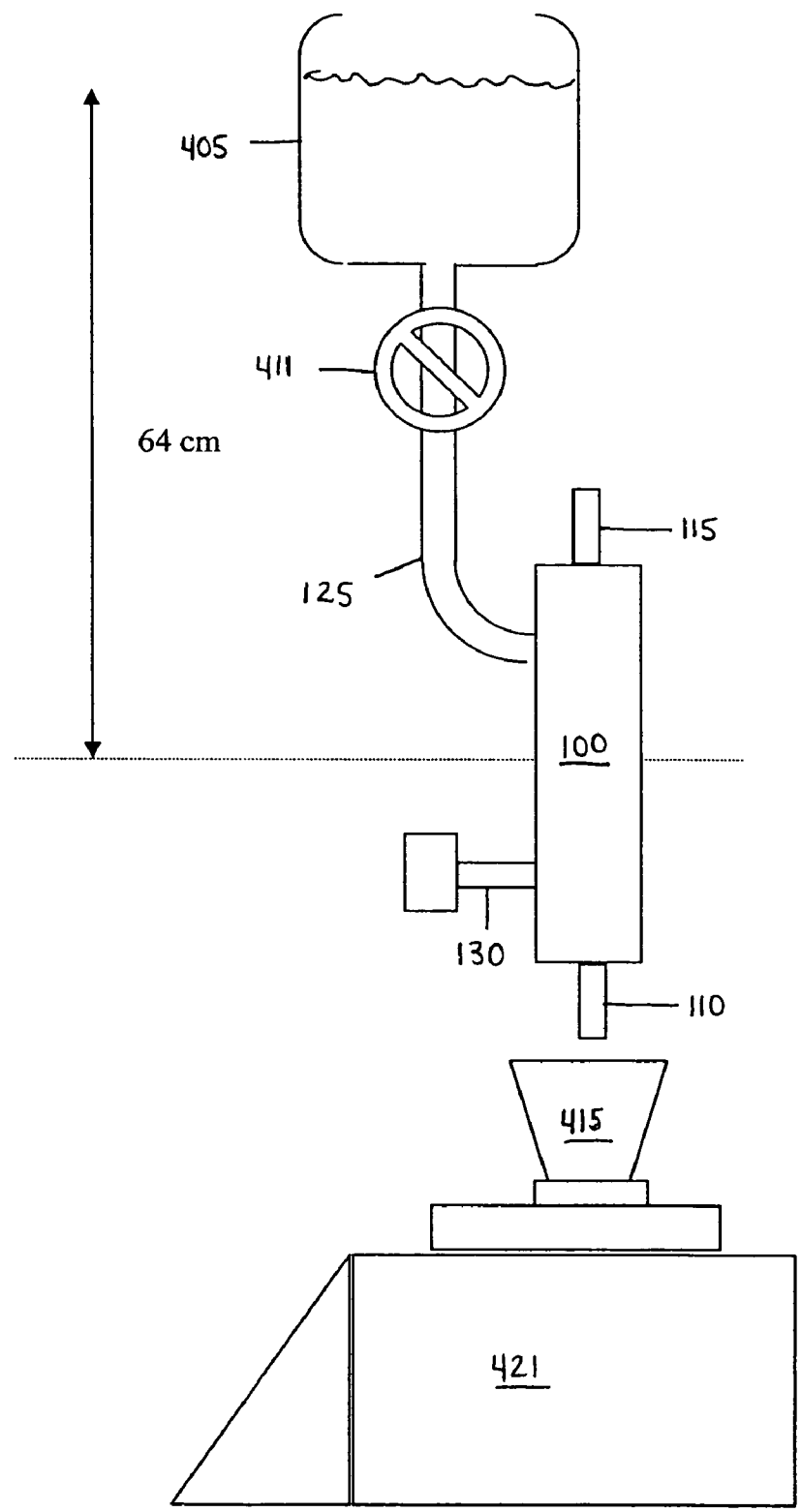
FIG. 4 is a schematic diagram of an embodiment of a test apparatus according to an aspect of this invention.

In order to determine whether a cartridge is optimized for delivery of vapor, "breakthrough" testing can be conducted. FIG. 4 illustrates breakthrough testing of cartridge 100, for example. Water pressure is applied to water jacket of cartridge 100 via side ports provided for water connections via water inlet 125 and water outlet 130. The pressure is determined by the height of water in water reservoir 405 above center of cartridge 100. Cartridge 100 is clamped above is sensitive electronic balance 421 reading to 0.1 gm. Any water that passes through walls of hollow fiber membranes 205 emerges from air outlet 110 and falls into container 415 placed on balance 421. Water delivery from water reservoir 405 to cartridge 100 via water inlet 125 is preferably controlled by manipulating a stopcock 411.

Referring to FIG. 4, the specified pressure for the test is 47 mmHg, which is equivalent to a water column of 64 cm of water. The height of water reservoir 405 is adjusted to 64 cm above the center of cartridge 100. The time for the first water drop to reach container 415 is recorded, as well as the rate of water collection in gm/hour over the first 30 minutes from breakthrough. Breakthrough occurs when a first water drop emerges from gas outlet 110.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A method for delivering heated and humidified gas to a patient, said method comprising the steps of:
    releasably connecting a fitting of a proximal end of a delivery tube to a supply unit;
    releasably coupling a nasal cannula to a distal end of the delivery tube;
    heating a humidification fluid in the supply unit;
    heating and humidifying a breathing gas in the supply unit separately from the heating of the humidification fluid, thereby producing a heated and humidified gas in the supply unit; and
    delivering the heated and humidified gas and the heated humidification fluid from the supply unit, through the delivery tube such that the heated humidification fluid heats the heated and humidified gas in the delivery tube, and to the nasal cannula for delivery to the patient.

2. A method of delivering a breathing gas to a patient, the method comprising the steps of:
    coupling a delivery tube to a supply unit;
    coupling a nasal cannula to the delivery tube;
    heating a humidification fluid in a heater in the supply unit;
    heating and humidifying the breathing gas in a humidifier in the supply unit;
    delivering the heated and humidified breathing gas from the supply unit to the delivery tube such that the heated and humidified breathing gas flows in a first direction through the delivery tube;
    heating the heated and humidified breathing gas with the humidification fluid in the delivery tube such that the humidification fluid flows from the heater, through the delivery tube, through the humidifier, and to the heater such that the fluid heats the heated and humidified breathing gas in the delivery tube and in the humidifier; and
    delivering the heated and humidified breathing gas from the delivery tube to the nasal cannula for delivery to the patient.

3. The method according to claim 2, further comprising the step of humidifying the breathing gas with the fluid.

4. The method according to claim 3, wherein humidifying the gas with the fluid is performed after the fluid insulates the breathing gas.

5. The method according to claim 2, further comprising flowing the fluid in a second direction, opposite the first direction, through the delivery tube.

6. A warming and humidifying system for a breathing gas comprising:
    a fluid supply;
    a means for heating the breathing gas with fluid from the fluid supply; and
    a means for humidifying the breathing gas with the fluid after the fluid has heated the breathing gas.

7. A system for delivering heated and humidified gas to a patient, the system comprising:
    a supply unit that heats a breathing gas and combines the breathing gas with water vapor to form a heated and humidified gas in the supply unit; and
    a delivery tube releasably coupled to the supply unit, the delivery tube being configured to transfer heat to the heated and humidified breathing gas received from the supply unit,
    wherein the breathing gas is humidified in the supply unit by fluid that has flowed through the delivery tube.

8. The system according to claim 7, wherein the supply unit provides fluid for humidifying the breathing gas.

9. The system according to claim 7, wherein the fluid flow through the system is configured such that the fluid heats the breathing gas prior to humidifying the breathing gas.

10. The system according to claim 7, further comprising a nasal cannula coupled to the delivery tube.

11. The system according to claim 10, wherein the nasal cannula is releasably coupled to the delivery tube.

12. A system for delivering humidified gas to a patient, said system comprising:
    a supply including:
        a water heater for heating a humidification fluid; and
        a humidifier having a breathing gas flow passage and a humidification fluid flow passage, the humidifier configured to heat and humidify a breathing gas in the breathing gas flow passage with the heated humidification fluid;
    a delivery tube assembly having a delivery tube with a proximal end and a distal end, said delivery tube assembly also having a fitting positioned at said proximal end of said delivery tube and releasably coupled to said supply unit, said delivery tube assembly configured to pass the heated humidification fluid from the water heater for delivery to the humidification fluid flow passage, to pass the heated and humidified gas received from the breathing gas flow passage, and to transfer heat from the heated humidification fluid to the heated and humidified gas received from said supply unit when coupled to said supply unit; and
    a nasal cannula releasably coupled to the distal end of the delivery tube to receive the heated and humidified gas passed by the delivery tube assembly.

13. The system recited in claim 12, said supply unit being configured to deliver humidified gas at a flow rate of about 1 liter per minute to about 8 liters per minute.

14. The system recited in claim 12, said supply unit being configured to deliver humidified gas at a flow rate above about 20 liters per minute.

15. The system recited in claim 12, further comprising a releasable coupling configured to couple said nasal cannula to said delivery tube assembly.

16. The system recited in claim 12, said releasable coupling comprising an adapter.

17. The system recited in claim 12, said fitting of said delivery tube assembly being configured for releasable connection to said supply unit.

18. The system recited in claim 12, said supply unit having a gas inlet configured to receive gas.

19. The system recited in claim 18, further comprising means for receiving gas from a source of gas and for delivering the gas to said gas inlet of said supply unit.

20. The system recited in claim 19, said gas receiving means comprising a tube.

21. The system recited in claim 20, said gas receiving means further comprising a fitting configured for connection to the source of gas.

22. The system recited in claim 12, said supply unit having a liquid inlet configured to receive supplemental liquid.

23. The system recited in claim 22, further comprising a source of supplemental liquid coupled to said liquid inlet.

24. The system recited in claim 23, said source of supplemental liquid comprising a water supply bag.

* * * * *